United States Patent [19]

Zenitz

[11] 4,005,093
[45] Jan. 25, 1977

[54] 2-NAPHTHYL-LOWER-ALKYLAMINES

[75] Inventor: Bernard L. Zenitz, Colonie, N.Y.

[73] Assignee: Sterling Drug Inc., New York, N.Y.

[22] Filed: Jan. 20, 1975

[21] Appl. No.: 542,546

[52] U.S. Cl. .................. 260/293.62; 260/239 B; 260/313.1; 260/326.5 C; 260/326.8; 260/570.5 P; 424/244; 424/267; 424/274
[51] Int. Cl.$^2$ .................................. C07D 211/14
[58] Field of Search ............... 260/293.62, 326.5 C, 260/239 B

[56] References Cited

UNITED STATES PATENTS

| 2,119,077 | 5/1938 | Hill et al. ................. 260/293.62 |
| 3,557,123 | 1/1971 | Kaiser et al. .............. 260/293.62 |
| 3,673,238 | 6/1972 | Elpern et al. .............. 260/293.62 |
| 3,886,168 | 5/1975 | Himmele et al. ............ 260/239 B |
| 3,894,002 | 7/1975 | Mackenzie et al. ......... 260/326.5 C |

OTHER PUBLICATIONS

Andrieux et al. Chem. Abst. 1966, vol. 65, Cols. 8837–8838.
Burke et al. Chem. Abst. 1953, vol. 47, Cols. 5408–5409.
Cohen et al. Chem. Abst. 1958, vol. 52, Cols. 7310–7312.
Duffin Chem. Abst. 1958, vol. 52, Cols. 12920–12921.
Emptoz et al. Chem. Abst. 1970, vol. 72, No. 66685v.
Foster et al. Chem. Abst. 1948, vol. 42, Cols. 983–984.
Hahn et al. Chem. Abst. 1967, vol. 66, No. 76898g.
Lee et al. J. Org. Chem. 1947 vol. 12, pp. 885–893.
N.V. Nederlandsche Combinatie voor Chemische Industrie Chem. Abst. 1960, vol. 54, Col. 1557.
Profft et al. Chem. Abst. 1962, vol. 57, Cols. 16550–16551.
Tseou et al. Chem. Abst. 1939, vol. 33, Cols. 5851–5852.
Sprague et al. Chem. Abst. 1962, vol. 55, col. 2104.
Fried et al. Chem. Abst. 1971, vol. 74, No. 87690z.

*Primary Examiner*—Natalie Trousof
*Attorney, Agent, or Firm*—William G. Webb; B. Woodrow Wyatt

[57] ABSTRACT

2-Naphthyl-lower-alkylamines, useful as anti-inflammatory agents, are prepared by reaction of a 2-naphthyl-lower-alkanoyl halide with an amine and reduction of the resulting 2-naphthyl-lower-alkanoylamine with a reagent effective to reduce an amide to an amine.

7 Claims, No Drawings

2-NAPHTHYL-LOWER-ALKYLAMINES

BACKGROUND OF THE INVENTION

1. Field of the Invention

This invention relates to 2-naphthyl-lower-alkylamines useful as anti-inflammatory agents.

2. Description of the Prior Art

A very large class of organic compounds of widely diverse structural types are known to be useful as anti-inflammatory agents, but many of such anti-inflammatory agents are acidic, for example α-(6-methoxy-2-naphthyl)propionic acid known generically as naproxen [Harrison et al., J. Med. Chem. 13, 203 (1970)]. Such acidic agents are often irritating, and in some cases are ulcerogenic, to the gastric mucosa when administered orally. There is thus a great need for anti-inflammatory agents, for example compounds having a basic amine function, which might be expected to be non-irritating to the gastric mucosa. Although the chemical literature describes numerous types of amine-substituted compounds asserted to have anti-inflammatory activity [see for example U.S. Pat. Nos. 3,770,748, patented Nov. 6, 1973 and 3,803,127, patented Apr. 9, 1974 (N-phenylpolymethyleneimines); U.S. Pat. Nos. 3,772,311, patented Nov. 13, 1973 and 3,773,772, patented Nov. 20, 1973 (polymethyleneimino-lower-alkanoylpyrazoles); U.S. Pat. No. 3,773,944, patented Nov. 20, 1973 (1-[3-aminopropyl]phthalans); U.S. Pat. No. 3,801,594, patented Apr. 2, 1974 (3-amino-lower-alkylindoles); and U.S. Pat. No. 3,810,985, patented May 14, 1974 (4-anilino-1,3,5-triazines)], no such basic compounds are presently known to be commercially available, and none are presently known to be under advanced investigation by pharmacologists for possible commercial development. The search for an effective, non-acidic anti-iflammatory agent for commercial development therefore continuous.

SUMMARY OF THE INVENTION

In one of its composition of matter aspects, the invention relates to certain 2-naphthyl-lower-alkylamines:

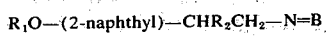

which are useful an anti-inflammatory agents.

In a second composition of matter aspect, the invention relates to certain 2-naphthyl-lower-alkanoylamines:

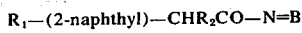

which are useful as intermediates for the preparation of the final products.

In a process aspect, the invention relates to a process for preparing the 2-naphthyl-lower-alkylamine final products from the intermediate 2-naphthyl-lower-alkanoylamines by reduction of the latter with reagents effective to reduce amides to amines, for example an alkali metal aluminum hydride, a trialkylaluminum or a dialkylaluminum hydride.

DETAILED DESCRIPTION INCLUSIVE OF THE PREFERRED EMBODIMENTS

More specifically, the invention relates to 2-naphthyl-lower-alkylamines which are useful as anti-inflammatory agents having the formula:

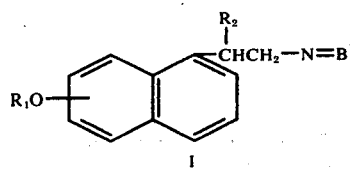

where $R_1$ and $R_2$ each represent hydrogen or lower-alkyl and N=B represents one of the groups

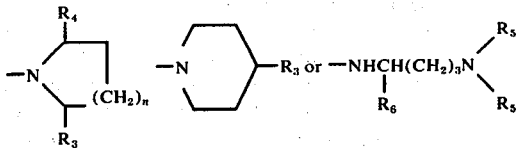

where $R_3$ represents lower-alkyl, cyclohexyl or cyclohexyl-lower-alkyl; $R_4$ and $R_6$ represent hydrogen or lower-alkyl; $R_5$ represents lower-alkyl; and $n$ represents one of the integers 1, 2 and 3.

Particularly preferred compounds within the ambit of the invention as described above are those having the formula:

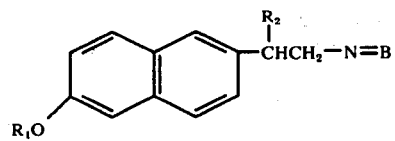

where $R_1$ represents lower-alkyl; $R_2$ represents hydrogen or lower-alkyl; and N=B has the meanings given above where $R_3$ represents cyclohexyl or cyclohexyl-lower-alkyl; $R_4$ represents hydrogen; $R_6$ represents lower-alkyl; and $n$ represents the integer 2.

As used herein, the term lower-alkyl means saturated, monovalent, aliphatic radicals, including branched-chain radicals, of from one to four carbon atoms, for example methyl, ethyl, propyl, isopropyl, butyl, sec.-butyl and isobutyl.

The compounds of formula I are prepared by reaction of an appropriate 2-naphthyl-lower-alkanoyl halide of formula III (prepared by reaction of the corresponding acid of formula II with a thionyl halide) with an appropriate amine of formula IV, H—N=B, and reduction of the resulting 2-naphthyl-lower-alkanoylamine of formula V with an alkali metal aluminum hydride. The method is represented by the following reaction sequence:

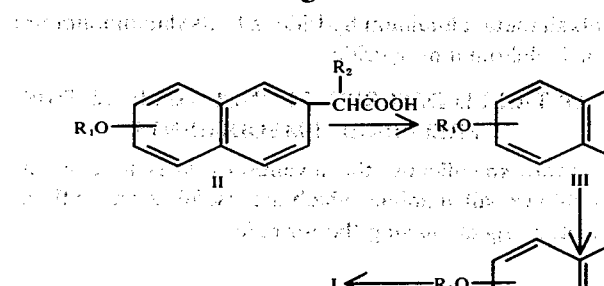

where $R_1$, $R_2$ and N=B have the meanings given above, and Hal represents halogen.

The preparation of the amides of formula V is essentially a "one-pot" reaction involving reaction of the acid of formula II with a thionyl halide in a non-protolytic organic solvent, for example benzene, toluene or xylene, at the reflux temperature thereof and addition of the acid halide, without isolation or further purification, either in the same solvent or in a different non-protolytic solvent, for example diethyl ether, dioxane or tetrahydrofuran, to a solution of the amine, H—N=B, in a non-protolytic organic solvent. The latter reaction is preferably carried out at ambient temperature and in the presence either of a molar excess of the amine or in the presence of an acid-acceptor, for example pyridine, a tri-lower-alkyl-amine, dimethylaniline or an alkali metal carbonate.

The amines of formula IV where N=B is the group:

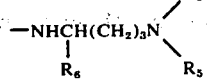

are known compounds.

The amines where —N=B is the group:

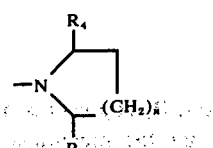

where $n$ is 2 are old, having been generally described in U.S. Pat. No. 3,238,215. As described therein, they are prepared by catalytic reduction over platinum oxide of appropriate 2-substituted (or 2,6-disubstituted) pyridines, which are commercially available.

The amines of formula IV where —N=B is the group

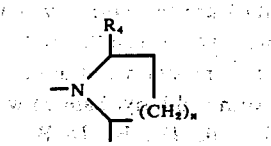

where $n$ is the integer 1 are prepared by refluxing a mixture of an appropriate alkanedione, ammonium acetate and glacial acetic acid, and catalytic reduction over platinum oxide of the resulting 2-$R_3$-5-$R_4$-pyrrole according to the reaction sequence:

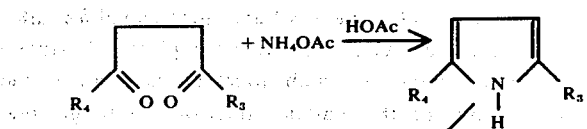

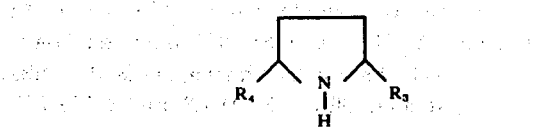

where $R_3$ and $R_4$ have the meanings given above.

Alternatively, the amines of formula IV where —N=B is the group:

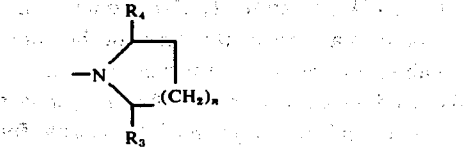

where $n$ is 1 are prepared by reaction of a Grignard reagent, $R_3$MgHal, with a 4-$R_4$-4-halobutyronitrile,

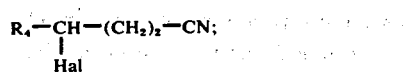

direct cyclization of the resulting 1-amino-1-$R_3$-4-$R_4$-4-halo-1-butene; and catalytic reduction of the resulting 2-$R_3$-5-$R_4$-4,5-dihydropyrrole as indicated by the reaction sequence:

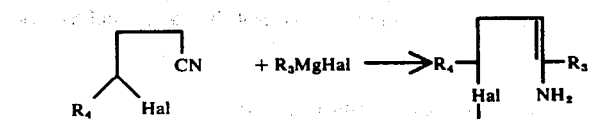

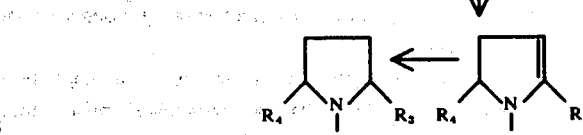

where $R_3$, $R_4$ and Hal have the meanings given above.

The amines of formula IV where —N=B is the group:

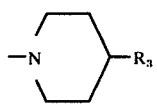

are advantageously prepared, like the amines where —N=B is the group:

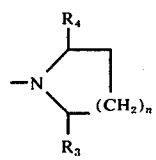

where n is 2, by catalytic reduction over platinum oxide of the corresponding 4-$R_3$-pyridine.

The 2-naphthyl-lower-alkanoic acids of formula II are a known class of compounds. (See for example Fried, U.S. Pat. No. 3,626,012, patented Dec. 7, 1971).

The novel compounds of the instant invention are the compounds of formula I and the acid-addition salts thereof. The compounds of formula I in free base form are converted to the acid-addition salt form by interaction of the base with an acid. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

It will thus be appreciated that formula I not only represents the structural configuraton of the bases of formula I but is also representative of the structural entity which is common to all of the compounds of formula I, whether in the form of the free base or in the form of the acid-addition salts of the base. It has been found that by virtue of this common structural entity, the bases and their acid-addition salts have inherent pharmacological activity of a type to be more fully described hereinbelow. This inherent phramacological activity can be enjoyed in useful form for pharmaceutical purposes by employing the free bases themselves or the acid-addition salts formed from pharmaceutically-acceptable acids, that is, acids whose anions are innocuous to the animal organism in effective doses of the salts so that beneficial properties inherent in the common structural entity represented by the free bases is not vitiated by side effects ascribable to the anions.

In utilizing this pharmacological activity of the salts of the invention, it is preferred, of course, to use pharmaceutically-acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salt with aqueous base as explained above, or alternatively, they can be converted to any desired pharmaceutically-acceptable acid-addiion salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purificaion salt derivatives can, if desired, be used to regenerate the pharmaceutically-acceptable free bases by reaction of the salts with aqueous base, or alternatively can be converted to a pharmaceutically-acceptable acid-addition salt by, for example, ion-exchange procedures.

It will be appreciated from the foregoing that all of the acid-addition salts of the new bases are useful and valuable compounds, regardless of considerations of solubility, toxicity, physical form, and the like, and are accordingly within the purview of the instant invention.

The novel feature of the compounds of the invention, then, resides in the concept of the bases and cationic forms of the new 2-naphthyl-lower-alkylamines and not in any particular acid moiety or acid anion associated with the salt forms of the compounds; rather, the acid moieties or anions which can be associated in the salt forms are in themselves neither novel nor critical and therefore can be any acid anion or acid-like substance capable of salt formation with the bases. In fact, in aqueous solutions, the base form or water-soluble acid-addition salt form of the compounds of the inventon both possess a common protonated cation or ammonium ion.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methane-sulfonic acid, isethionic acid, benzenesulfonic acid, p-toluene-sulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared by reacting the free base and acid in an organic solvent and isolating the salt directly or by concentration of the solution.

Due to the presence of at least one and as many as three asymmetric centers in the compunds of the invention (i.e. the carbon atom of the group —N=B to which the group $R_3$ is attached, the carbon adjacent the secondary nitrogen atom of the group —N=B when $R_6$ is lower-alkyl in the group

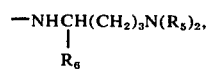

and the carbon atoms to which the groups $R_2$ and $R_4$ are attached when other than hydrogen), the compounds of the invention can exist in sterochemically isomeric forms, which are all considered to be within the purview of the invention. If desired, the isolation or the production of a particular stereochemical form can be accomplished by application of general principles known in the art.

In standard pharmacological test procedures, the compounds of formula I have been found to possess anti-inflammatory activity and are useful as anti-inflammatory agents. Anti-inflammatory activity was determined using (1) the inhibition of carrageenin-induced foot edema test essentially described by Van Arman et al., J. Pharmacol. Exptl. Therap. 150, 328 (1965) as modified by Winter et al., Proc. Soc. Exp. Biol. and Med. 111, 544 (1962) and (2) a modification of the inhibition of adjuvant-induced arthritis test described by Pierson, J. Chronic Diseases 16, 863 (1963) and Glenn et al., Am. J. Vet. Res. 26, 1180 (1965).

The compounds of the invention can be prepared for use by incorporating them in unit dosage form as tablets or capsules for oral administration either alone or in combination with suitable adjuvants such as calcium carbonate, starch, lactose, talc, magnesium stearate, gum acacia, and the like. Still further, the compounds can be formulated for oral administration in aqueous alcohol, glycol or oil solutions or oil-water emulsions in the same manner as conventional medicinal substances are prepared.

The molecular structures of the compounds of the invention were assigned on the basis of study of their infrared, ultraviolet and NMR spectra, and confirmed by the correspondence between calculated and found values for elementary analysis for the elements.

The following examples will further illustrate the invention without, however, limiting it thereto. All melting points are uncorrected.

Preparation of Amine Intermediates

Preparation 1

In three separate runs, 33.8 g. (0.20 mole) portions of 2-benzylpyridine, each in a solution of about 225 ml. of ethanol and 22 ml. of concentrated hydrochloric acid, were reduced over 4.0 g. portions of platinum oxide catalyst under about 54 p.s.i. of hydrogen at a temperature of about 55°–61° C. When reduction was complete in each case, the catalyst was removed by filtration, washed with small portions of ethanol, and the combined filtrates evaporated to a volume of about 80 ml. and diluted to approximately 500 ml. with boiling acetone. The solid which precipitated was collected, washed with acetone and dried giving a combined yield of 124.8 g. of 2-cyclohexylmethylpiperidine hydrochloride, m.p. 211°–213° C. The free base was regenerated from the hydrochloride by neutralization of an aqueous solution of the latter with potassium carbonate, extraction of the oily base into benzene, evaporation of the benzene solution to dryness, and distillation of the residual oil in vacuo at 55°–59° C./0.27 mm. There was thus obtained 89.4 g. of 2-cyclohexylmethylpiperidine.

Preparation 2

A mixture of 15.52 g. (0.10 mole) of 2-phenylpyridine, 15 ml. of concentrated hydrochloric acid and 2.0 g. of platinum oxide in 185 ml. of ethanol in a pressure bottle was heated and shaken in a Parr hydrogenator under 55 p.s.i. of hydrogen at a temperature around 60° C. When reduction was complete in about 8 hours, the catalyst was removed by filtration and the filtrate concentrated to about 50 ml. and diluted with 200 ml. of acetone. The solid which separated was collected and dried to give 14.54 g. of 2-cyclohexylpiperidine hydrochloride, m.p. 251°–253° C.

Preparation 3

A mixture of 9.1 g. (0.05 mole) of 2-stilbazole (Shaw et al., J. Chem. Soc. 1933, 77–79) and 1.0 g. of platinum oxide in a solution of 240 ml. of ethanol and 10 ml. of concentrated hydrochloric acid in a pressure bottle was heated and shaken on a Parr hydrogenator under about 55 p.s.i. of hydrogen at a temperature of about 60° C. When reduction was complete in about 8 hours, the catalyst was removed by filtration, the filtrate concentrated to a volume of about 50 ml. and diluted with about 200 ml. of acetone. The solid which separated was collected and dried to give 9.6 g. of 2-(2-cyclohexylethyl)piperidine hydrochloride, m.p. 155°–156° C.

Preparatin 4

A solution of 78.1 g. (0.84 mole) of 4-methylpyridine and 89.0 g. (0.84 mole) of benzaldehyde in 103 g. of acetic anhydride was heated with stirring under reflux for 24 hours. The mixture was then concentrated to a thick oil in vacuo and the residue dissolved in hot ethanol. The solid which separated was collected and recrystallized from ethanol to give 57.9 g. of 4-styrylpyridine, m.p. 131.5°–133° C.

The latter (36.2 g., 0.2 mole), dissolved in 220 ml. of absolute ethanol and 30 ml. of concentrated hydrochloric acid, was reduced over 3.0 g. of platinum oxide under a hydrogen pressure of about 55 p.s.i. The product was worked up in the manner described above in Preparation 1 and isolated in the form of the hydrochloride salt to give 43.5 g. of 4-(2-cyclohexylethyl)-piperidine hydrochloride, m.p. 246°–248° C.

Preparation 5

4-Phenylpyridine (15.5 g., 0.1 mole) dissolved in 185 ml. of absolute ethanol and 15 ml. of concentrated hydrochloric acid was reduced with hydrogen over 2 g. of platinum oxide under a hydrogen pressure of about 55 p.s.i. The product was worked up in the manner described above in Preparation 1 and isolated in the form of the hydrochloride. (The free base gives m.p. 106°–109° C.)

Preparation 6

To a mixture of 8.6 g. (0.36 mole) of magnesium turnings in 150 ml. of dry ether was added in small portions with cooling and stirring a solution of 45.0 g. (0.36 mole) of benzyl chloride in 75 ml. of anhydrous ether. When addition was complete, the mixture was stirred for about 1 hour and then treated dropwise with a solution of 26.6 g. of 4-chlorobutyronitrile in 95 ml. of ether. When addition was complete, the ether was gradually distilled off while replacing with an equal volume of toluene. The mixture was heated under reflux (at about 109° C.) for about 30 minutes, cooled to about 15° C., treated dropwise with 300 ml. of 10% aqueous ammonium chloride, filtered, and the organic layer separated. The latter was washed with three 100 ml. portions of dilute hydrochloric acid, and the combined acid extracts were basified with solid potassium carbonate. Extraction of the mixture with ether and removal of the solvent from the combined organic extracts afforded an oil which was distilled in vacuo to give 13.05 g. of 2-benzyl-4,5-dihydropyrrole, b.p. 123°–125° C./13 mm., $n_d^{25}$ 1.5405.

The latter, dissolved in 210 ml. of ethanol and 15 ml. of concentrated hydrochloric acid was reduced with hydrogen over 2 g. of platinum oxide under a hydrogen pressure of about 50 p.s.i. The mixture was worked up in the manner described above in Preparation 1 and the product isolated in the form of the hydrochloride salt to give 16.8 g. of 2-cyclohexylmethyl-pyrrolidine hydrochloride, m.p. 130.5°–131.5° C. (from acetone).

Preparation 7

To a suspension of 11.2 g. (1.6 mole) of lithium wire in 600 ml. of anhydrous ether was added dropwise 125.6 g. (0.8 mole) of bromobenzene. When addition was complete, the mixture was stirred for about a half hour and then treated dropwise first with a solution of 74.4 g. (0.8 mole) of picoline in 100 ml. of anhydrous ether and then, after stirring for 15 minutes, with a solution of 74.0 g. (0.4 mole) of 2-phenylethyl bromide in 100 ml. of ether. The mixture was stirred at ambient temperature for about 12 hours and then poured with stirring onto 300 g. of ice. When all excess lithium had reacted, the layers were separated, the aqueous layer washed with additional ether, and the combined organic portions were washed with brine, dried and taken to dryness to give a residual oil which was distilled in vacuo to give 41.3 g. of 2-(3-phenylpropyl)pyridine, b.p. 76°–78° C./0.05 mm., $n_D^{25}$ 1.5592.

The latter (19.7 g., 0.1 mole) dissolved in 235 ml. of ethanol and 15 ml. of concentrated hydrochloric acid was reduced with hydrogen over 2 g. of platinum oxide under a hydrogen pressure of around 55 p.s.i. at about 65° C. The product was worked up in the manner described above in Preparation 1 and isolated in the form of the hydrochloride salt to give 22.2 g. of 2-(3-cyclohexylpropyl)piperidine hydrochloride, m.p. 175°–176.5° C. (from ethyl acetate).

Preparation 8

Reduction of 2-ethyl-6-methylpyridine [Lanin, J. Applied Chem. (U.S.S.R.) 16, 388-93 (1943); Chem. Abs. 38, 6522⁴ (1944)] with hydrogen over a platinum oxide catalyst in an acid medium affords 2-ethyl-6-methylpiperidine.

Preparation of Final Products

EXAMPLE 1

A solution of 50 g. (0.22 mole) of d,1-α-(6-2-naphthyl)propionic acid and 140 ml. of thionyl chloride in 700 ml. of benzene was refluxed for 3 and a half hours and then taken to dryness in vacuo. The residual oil consisting of crude d,1-α-(6-methoxy-2-naphthyl)propionyl chloride was dissolved in 250 ml. of anhydrous diethyl ether and added dropwise with stirring to a solution of 44 g. (0.24 mole) of d,1-2-cyclohexylmethylpiperidine and 26.5 g. (0.26 mole) of triethylamine in 500 ml. of anhydrous diethyl ether over a period of 45 minutes. The mixture was then stirred at ambient temperature for about 12 hours and filtered. The filtrate was washed once with dilute hydrochloric acid, once with water, once with dilute potassium carbonate, once again with water, dried and taken to dryness to give 85 g. of 2-cyclohexylmethyl-1-[α-(6-methoxy-2-naphthyl)propionyl]piperidine as an orange oil.

The latter (0.22 mole), dissolved in 500 ml. of anhydrous diethyl ether, was added dropwise with stirring to a suspension of 16.5 g. (0.44 mole) of lithium aluminum hydride in 300 ml. of ether. When addition was complete, the mixture was stirred at ambient temperature for about 12 hours and then decomposed by the dropwise addition of a solution of 30 ml. of water in 150 ml. of tetrahydrofuran. The mixture was filtered, the filter washed with ether, and the combined filtrate and wash concentrated to dryness. The residual oil was dissolved in 500 ml. of ether, acidified with ethereal hydrogen chloride, and the gum which separated was dissolved in hot acetone, cooled and the solution diluted with ether. The solid which separated was collected and dried to give 37 g. of 2-cyclohexylmethyl-1-[2-(6-methoxy-2-naphthyl)-2-methylethyl]piperidine hydrochloride, m.p. 198°–199° C., designated the α-isomer, $\alpha_D$=0° (1% CHCl₃).

The mother liquor from the above crystallization of the α-isomer was taken to dryness and the residue recrystallized from isopropyl acetate to give 8.0 g. of an isomeric hydrochloride, m.p. 168°–169° C. designated the β-isomer, $\alpha_D$=0° (1% CHCl₃). Mixed melting point with the α-isomer described above gave m.p. 161°–179° C.

d,1-α-(6-Methoxy-2-naphthyl)propionic acid was resolved with 1-cinchonidine using the procedure described by Harrison et al., J. Med. Chem. 13, 203–205 (1970), and the d-isomer ($\alpha_D$=+65.9) thus obtained (6.8 g., 0.03 mole) was converted to 2-cyclohexylmethyl-1-[2-(6-methoxy-2-naphthyl)-2-methylethyl]-piperidine hydrochloride via the corresponding acid chloride and amide using the procedure described above for the preparation of the α-isomer. The crude product, in the form of the hydrochloride salt, was recrystallized from acetone/ether to give 5.6 g. of material having m.p. 191.5°–193° C., designated the γ-isomer $\alpha_D$=−4.8° (1% CHCl₃). Mixed melting point with the α-isomer described above gave m.p. 186°–188° C.

EXAMPLES 2–11

Following a procedure similar to that described above in Example 1, the following compounds of formula I are prepared:

EXAMPLE 2

2-cyclohexyl-1-[2-(6-methoxy-2-naphthyl)-2-methylethyl-]piperidine hydrochloride, m.p. 145° C. (foams), recrystallized from acetone/ether, prepared by reaction of d,1-α-(6-methoxy-2-naphthyl)-propionyl chloride with d,1-2-cyclohexylpiperidine and reduction of the resulting 2-cyclohexyl-1-[α-(6-methoxy-2-naphthyl)propionyl]piperidine with lithium aluminum hydride;

EXAMPLE 3

2-(2-cyclohexylethyl)-1-[2-(6-methoxy-2-naphthyl)-2-methylethyl]-piperidine hydrochloride, m.p. 78°–82° C., recrystallized from benzene, prepared by reaction of d,1-α-(6-methoxy-2-naphthyl)-propionyl chloride with d,1-2-(2-cyclohexylethyl)piperidine and reduction of the resulting 2-(2-cyclohexylethyl)-1-[α-(6-methoxy-2-naphthyl)propionyl]piperidine with lithium aluminum hydride;

EXAMPLE 4

4-(2-cyclohexylethyl)-1-[2-(6-methoxy-2-naphthyl)-2-methylethyl]-piperidine, m.p 108°–111° C., recrystallized from methanol, prepared by reaction of d,1-α-(6-methoxy-2-naphthyl)propionyl chloride with d,1-4-(2-cyclohexylethyl)piperidine and reduction of the resulting 4-(2-cyclohexylethyl)-1-[α-(6-methoxy-2-naphthyl)-propionyl]piperidine with lithium aluminum hydride;

EXAMPLE 5

2-cyclohexylmethyl-1-[2-(6-methoxy-2-naphthyl)ethyl]piperidine, m.p. 28°–31° C., prepared by reaction of (6-methoxy-2-naphthyl)-acetyl chloride with d,1-2-cyclohexylmethylpiperidine and reduction of the resulting 2-cyclohexylmethyl-1-[(6-methoxy-2-naphthyl)-acetyl]piperidine, m.p. 77°–79° C. (from hexane) with lithium aluminum hydride;

EXAMPLE 6

N-[2-(6-methoxy-2-naphthyl)-2-methylethyl]-N-[5-(N',N'-diethyl-amino)-2-pentyl]amine, yellow oil, prepared by reaction of d,1-α-(6-methoxy-2-naphthyl)-propionyl chloride with 5-(N',N'-diethyl-amino)-2-pentylamine and reduction of the resulting N-[α-(6-methoxy-2-naphthyl)propionyl]-N-[5-(N',N'-diethylamino)-2-pentyl]amine with lithium aluminum hydride;

EXAMPLE 7

4-cyclohexyl-1-[2-(5-methoxy-2-naphthyl)ethyl]-piperidine prepared by reaction of (6-methoxy-2-naphthyl)acetyl chloride with 4-cyclohexylpiperidine and reduction of the resulting 4-cyclohexyl-1-[(5-methoxy-2-naphthyl)acetyl]piperidine with lithium aluminum hydride;

EXAMPLE 8

2-cyclohexylmethyl-1-[2-(7-methoxy-2-naphthyl)-2-methylethyl]-pyrrolidine prepared by reaction of d,1-α-(7-methoxy-2-naphthyl)-propionyl chloride with 2-cyclohexylmethylpyrrolidine and reduction of the resulting 2-cyclohexylmethyl-1-[α(7-methoxy-2-naphthyl)propionyl]pyrrolidine with lithium aluminum hydride;

EXAMPLE 9

2-ethyl-6-methyl-1-[2-(6-methoxy-2-naphthyl)-2-methylethyl]-piperidine prepared by reaction of d,1-α-(6-methoxy-2-naphthyl)-propionyl chloride with 2-ethyl-6-methylpiperidine and reduction of the resulting 2-ethyl-6-methyl-1-[α-(6-methoxy-2-naphthyl)-propionyl]-piperidine with lithium aluminum hydride;

EXAMPLE 10

2-(3-cyclohexylpropyl)-1-[2-(6-methoxy-2-naphthyl)-2-methylethyl]-piperidine prepared by reaction of d,1-α-(6-methoxy-2-naphthyl)-propionyl chloride with 2-(3-cyclohexylpropyl)piperidine and reduction of the resulting 2-(3-cyclohexylpropyl)-1-[α-(6-methoxy-2-naphthyl)-propionyl]-piperidine with lithium aluminum hydride;

EXAMPLE 11

2-methyl-1-[2-(6-methoxy-2-naphthyl)-2-methylethyl]hexamethylene-imine prepared by reaction of d,1-α-(6-methoxy-2-naphthyl)-propionyl chloride with 2-methylhexamethyleneimine and reduction of the resulting 2-methyl-1-[α-(6-methoxy-2-naphthyl)-propionyl]hexamethyleneimine with lithium aluminum hydride.

EXAMPLE 12

Heating a solution of 2-cyclohexylmethyl-1-[2-(6-methoxy-2-naphthyl)-2-methylethyl]piperidine in aqueous hydrobromic acid and isolation of the product from a neutral medium affords 2-cyclohexylmethyl-1-[2-(6-hydroxy-2-naphthyl)-2-methylethyl]piperidine.

The 2-naphthyl-lower-alkylamines of formula I of the invention have been tested in the carrageenin edema (CE) and adjuvant arthritis (AA) tests and found to have anti-inflammatory activity. Data so-obtained, given in terms of percent inhibition at a dose expressed in terms of millimoles ($\mu$M)/kg., are given below. All data were obtained on oral administration.

| Example | CE (% Inhib./$\mu$M/kg.) | AA (% Inhib./$\mu$M/kg.) |
|---|---|---|
| 1 (α-Isomer) | 14%/0.08 | 0%/0.01 |
|  | 40%/0.324 | 8%/0.04 |
|  |  | 86%/0.16 |
| 1 (β-Isomer) | 16%/0.08 | 0%/0.01 |
|  | 47%/0.324 | 12%/0.04 |
|  |  | 89%/0.16 |
| 1 (γ-Isomer) | 24%/0.08 | 2%/0.018 |
|  | 45%/0.324 | 49%/0.053 |
|  |  | 86%/0.16 |
| 2 | 35%/0.08 | 17%/0.01 |
|  | 69%/0.324 | 31%/0.04 |
|  |  | 61%/0.16 |
| 3 | 66%/0.08 | 0%/0.005 |
|  | 52%/0.324 | 40%/0.02 |
|  |  | 16%/0.08 |
| 4 | 22%/0.08 | 0%/0.005 |
|  | 38%/0.324 | 0%/0.02 |
|  |  | 34%/0.08 |
| 5 | 29%/0.08 | 55%/0.324 |
|  | 68%/0.324 |  |
| 6 | 28%/0.08 | 73%/0.16 |
|  | 26%/0.324 |  |

I claim:

1. A member of the group consisting of (A) compounds having the formula:

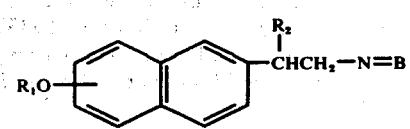

where $R_1$ and $R_2$ each represent hydrogen or lower-alkyl and N=B represents one of the groups

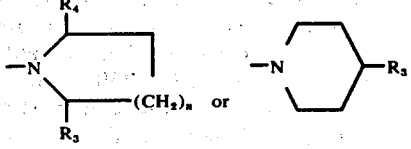

where $R_3$ represents lower-alkyl, cyclohexyl or cyclohexyl-lower-alkyl; $R_4$ represents hydrogen or lower-alkyl; and $n$ represents one of the integers 1, 2 and 3 and (B) pharmaceutically acceptable acid-addition salts thereof.

2. A member of the group consisting of (A) compounds according to claim 1 having the formula

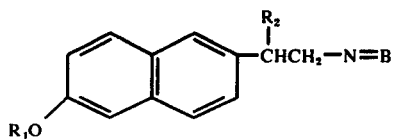

where R₁ represents lower-alkyl; R₂ represents hydrogen or lower-alkyl; and N=B represents one of the groups

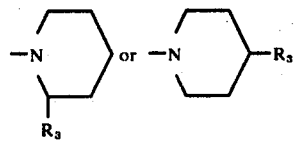

where R₃ represents cyclohexyl or cyclohexyl-loweralkyl and (B) pharmaceutically acceptable acid-addition salts thereof.

3. 2-Cyclohexylmethyl-1-[2-(6-methoxy-2-naphthyl)-2-methylethyl]piperidine hydrochloride according to claim 2.

4. 2-Cyclohexyl-1-[2-(6-methoxy-2-naphthyl)-2-methylethyl]piperidine hydrochloride according to claim 2.

5. 2-(2-Cyclohexylethyl)-1-[2-(6-methoxy-2-naphthyl)-2-methylethyl]piperidine hydrochloride according to claim 2.

6. 4-(2-Cyclohexylethyl)-1-[2-(6-methoxy-2-naphthyl)-2-methylethyl]piperidine according to claim 2.

7. 2-Cyclohexylmethyl-1-[2-(6-methoxy-2-naphthyl)-ethyl]piperidine according to claim 2.

* * * * *

UNITED STATES PATENT AND TRADEMARK OFFICE
CERTIFICATE OF CORRECTION

PATENT NO. : 4,005,093

DATED : January 25, 1977

INVENTOR(S) : Bernard L. Zenitz

It is certified that error appears in the above-identified patent and that said Letters Patent are hereby corrected as shown below:

Column 1, line 42, change "anti-iflammatory" to read --anti-inflammatory--.

Column 1, line 43, change "continuous" to read --continues--.

Column 5, line 68, change "addiion" to read -- addition --

Column 6, line 58, chanage "compunds" to read -- compounds --.

Column 7, line 33, change "analysis" to read -- analyses -

Column 8, line 23, change "Preparatin" to read -- Preparation --.

UNITED STATES PATENT AND TRADEMARK OFFICE
CERTIFICATE OF CORRECTION

PATENT NO. : 4,005,093
DATED : January 25, 1977
INVENTOR(S) : Bernard L. Zenitz

It is certified that error appears in the above-identified patent and that said Letters Patent are hereby corrected as shown below:

Column 1, line 58 change "$R_1$-(2-naphthyl)-$CHR_2$CO-N=B" to read --$R_1$O-(2-naphthyl)-$CHR_2$CO-N=B--.

Column 2, line 15, Formula I should read:

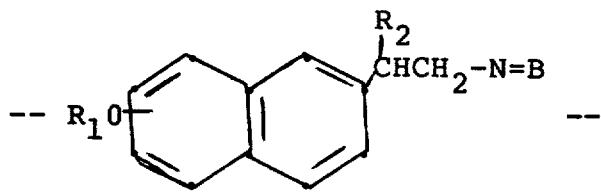

Column 5, line 48 change "phramacological" to read --pharmacological--.

Signed and Sealed this

Twenty-seventh Day of April 1982

|SEAL|

Attest:

GERALD J. MOSSINGHOFF

Attesting Officer    Commissioner of Patents and Trademarks